US008622653B2

(12) United States Patent
Lipes et al.

(10) Patent No.: US 8,622,653 B2
(45) Date of Patent: Jan. 7, 2014

(54) APPARATUS AND METHOD FOR STERILIZING SEED BEDS IN SOIL

(76) Inventors: Arnold Lipes, Montreal (CA); Pierre-André Daignault, Blainville (CA)

( * ) Notice: Subject to any disclaimer, the term of this patent is extended or adjusted under 35 U.S.C. 154(b) by 283 days.

(21) Appl. No.: 13/104,124

(22) Filed: May 10, 2011

(65) Prior Publication Data

US 2012/0288333 A1   Nov. 15, 2012

(51) Int. Cl.
  *A01G 11/00* (2006.01)
  *A01G 13/02* (2006.01)

(52) U.S. Cl.
  USPC ............. 405/128.6; 405/128.85; 47/DIG. 10; 126/271.2; 239/130; 239/135; 239/147; 239/159; 239/172; 404/77; 111/120

(58) Field of Classification Search
  USPC ..................... 111/120, 200, 900; 47/1.44, 2; 37/227–230; 43/144; 126/271.1, 271.3; 239/128–139, 146–176; 404/77, 79; 405/128.1–128.9
  See application file for complete search history.

(56) References Cited

U.S. PATENT DOCUMENTS

| 2,272,190 | A | 2/1942 | Elliott |
| 4,632,044 | A | 12/1986 | Allen |
| 5,259,327 | A | 11/1993 | Thompson, Jr. et al. |
| 5,287,818 | A | 2/1994 | Rajamannan |
| 5,430,970 | A | 7/1995 | Thompson et al. |
| 5,622,123 | A | 4/1997 | Rajamannan |
| 5,624,635 | A | 4/1997 | Pryor |

FOREIGN PATENT DOCUMENTS

JP           03259021 A   *  11/1991

* cited by examiner

*Primary Examiner* — Christopher J Novosad
(74) *Attorney, Agent, or Firm* — Norton Rose Fulbright Canada LLP

(57) ABSTRACT

An apparatus and a method are described for sterilizing seed beds in soil. The apparatus is comprised of at least one hot water injecting chamber defined by a pair of spaced-apart side walls secured to one another and defining therebetween a passage. A plurality of jet holes are provided in an inner surface of each of the side walls and facing the direction of the passage. The jet holes communicate with a manifold associated with each side wall which is connected to a supply of pressurized hot water. Each of the side walls is configured to penetrate into the soil in at least a lower region thereof whereby to inject into the soil in the passage between the pair of plates the pressurized hot water as the hot water injecting chamber is displaced in the soil.

14 Claims, 4 Drawing Sheets

APPARATUS AND METHOD FOR STERILIZING SEED BEDS IN SOIL

TECHNICAL FIELD

The present invention relates to an apparatus and method for sterilizing seed beds in soil by injecting hot pressurized water under the soil surface between a pair of spaced-apart side walls displaceable in the soil to form a seed bed rid of weeds between the side walls.

BACKGROUND ART

It has long been known that by injecting hot pressurized water or steam within a soil that unwanted seeds or weeds can be destroyed whereby to create planting beds. For example it is described in U.S. Pat. No. 2,272,190 issued on Feb. 10, 1942 that soil can be sterilized by injecting super heated steam into the soil as a means of killing or destroying weed seeds, insect eggs, larva and pests. In that patent a ground furrowing implement is used which is pulled by tractor and steam is injected in the soil which is loosened by plough discs. The steam generating unit utilizes a very large boiler which has a fire box to generate super heated steam which is directed by pipes for discharge into the loosened soil behind the plough discs. Because this assembly causes the soil to be disturbed in a random fashion by pipes while steam is injected therein it has been found to be insufficient to provide clean seeding beds void of weeds or unwanted growth for future plantings.

U.S. Pat. No. 5,622,123 also relates to a process and apparatus for killing soil pathogens and it also utilizes stirrer tools which penetrate into the ground surface for mixing the soil and injecting hot water and wherein a foam is applied over the disturbed soil to provide an insulation whereby the heat from the hot water is being retained within the soil to disturb weeds. Again, this system disturbs the soil and uses foam to prevent rapid dissipation of the heat injected into the soil in an attempt to control the pathogenic organisms in the soil and particularly weed seeds. This apparatus uses a soil tilling feature which does not provide for the creation of clean seeding beds devoid of weeds.

SUMMARY OF INVENTION

It is a feature of the present invention to provide an apparatus and method for sterilizing soil and which substantially overcomes the above-mentioned disadvantages of the prior art.

Another feature of the present invention is to provide an apparatus for sterilizing soil and which apparatus comprises a hot water injection chamber defined by a pair of spaced-apart adjustable side walls having jet holes facing inwardly into a passage defined between the spaced-apart side walls to inject pressurized hot water under the top surface of a soil to form a seed bed by displacing the hot water injecting chamber over the soil.

A further feature of the present invention is to provide an apparatus for sterilizing soil comprising at least two or more hot water injecting chambers adjustably supported in spaced-apart horizontal and vertical planes under a carriage displaceable over the soil to form thereunder, as it is displaced, two or more sterilized seeding beds.

According to a further feature of the present invention there is provided a method of sterilizing soil to destroy unwanted growth in a planting bed being formed in the soil by displacing at least one hot water injecting chamber having spaced-apart side walls and penetrated into the soil at a lower end thereof and having jet holes in the inner face of each of the spaced-apart side walls of each injecting chamber to inject hot water into the soil to destroy unwanted growth.

According to the above features, from a broad aspect, the present invention provides an apparatus for sterilizing soil. The apparatus comprises at least one hot water injecting chamber defined by a pair of spaced-apart side walls secured to one another in defining therebetween an open-ended passage. A plurality of jet holes are provided in an inner surface of each of the side walls and facing in the direction of the passage. The jet holes communicate with a manifold connectable to a supply of pressurized hot water. Each of the side walls are configured to penetrate into the soil in at least in a lower region thereof whereby to inject into the soil in the passage between the pairs of plates the pressurized hot water as the hot water injecting chamber is displaced in the top surface of the soil.

According to the above features, from a broad aspect, the present invention also provides a method of sterilizing soil to destroy unwanted growth in a planting bed being formed in the soil. The method comprises providing an apparatus as defined in the previous paragraph. Water is heated in a hot water generator to a temperature in the range of about 150° F. to 200° F. The apparatus is displaced in the top surface of the soil to create the planting bed with the hot water injecting chamber penetrating into the soil while injecting under pressure the hot water into the planting bed from opposed sides thereof to destroy weeds, seeds or roots of unwanted growth in the bed being formed.

BRIEF DESCRIPTION OF DRAWINGS

A preferred embodiment of the present invention will now be described with reference to the accompanying drawings in which.

DESCRIPTION OF PREFERRED EMBODIMENTS

Figure 1A:
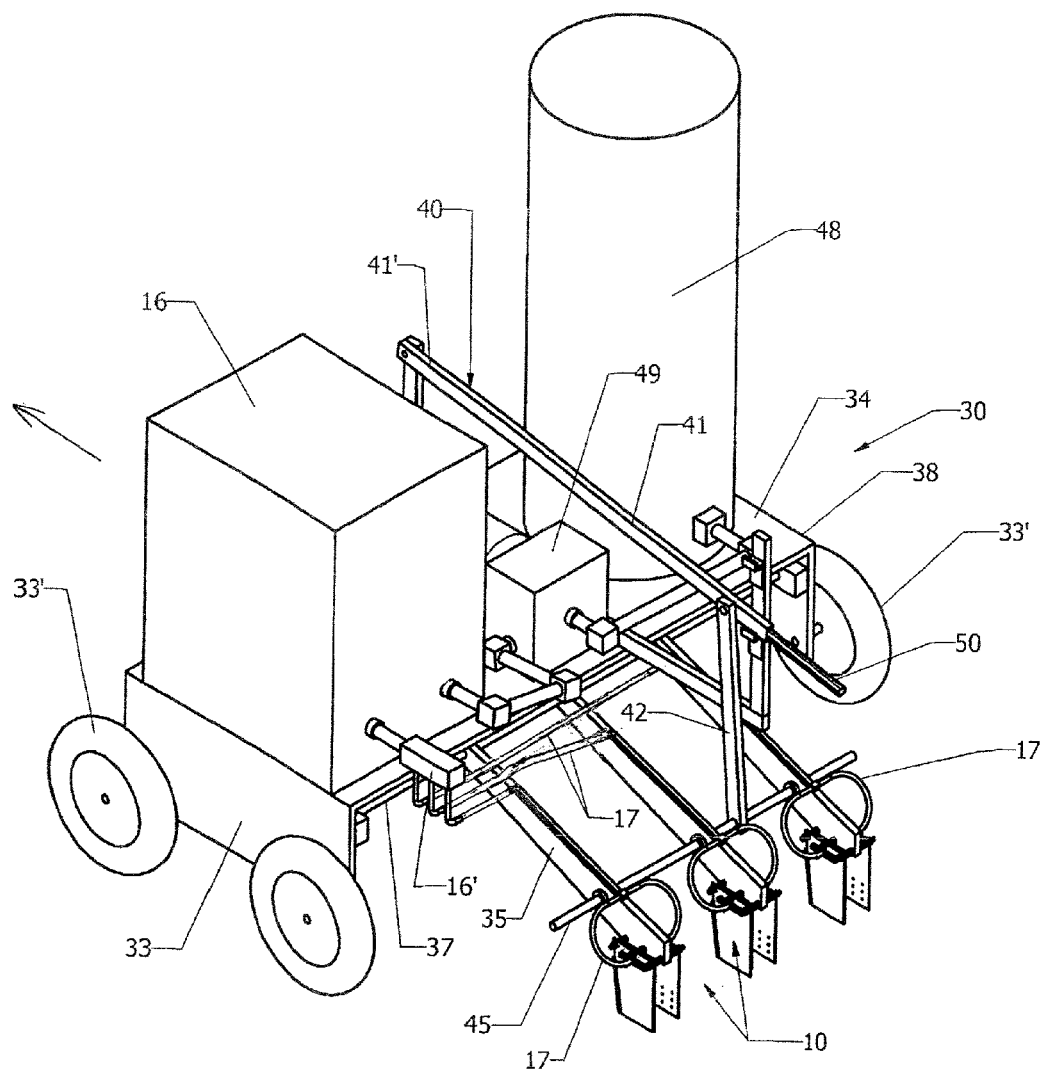
FIGS. 1A and 1B are a perspective view of an apparatus constructed in accordance with the present invention for sterilizing soil to create sterile soil beds free of unwanted growths in the soil and as herein illustrated the apparatus is mounted on a displaceable carriage.
Figure 1B:
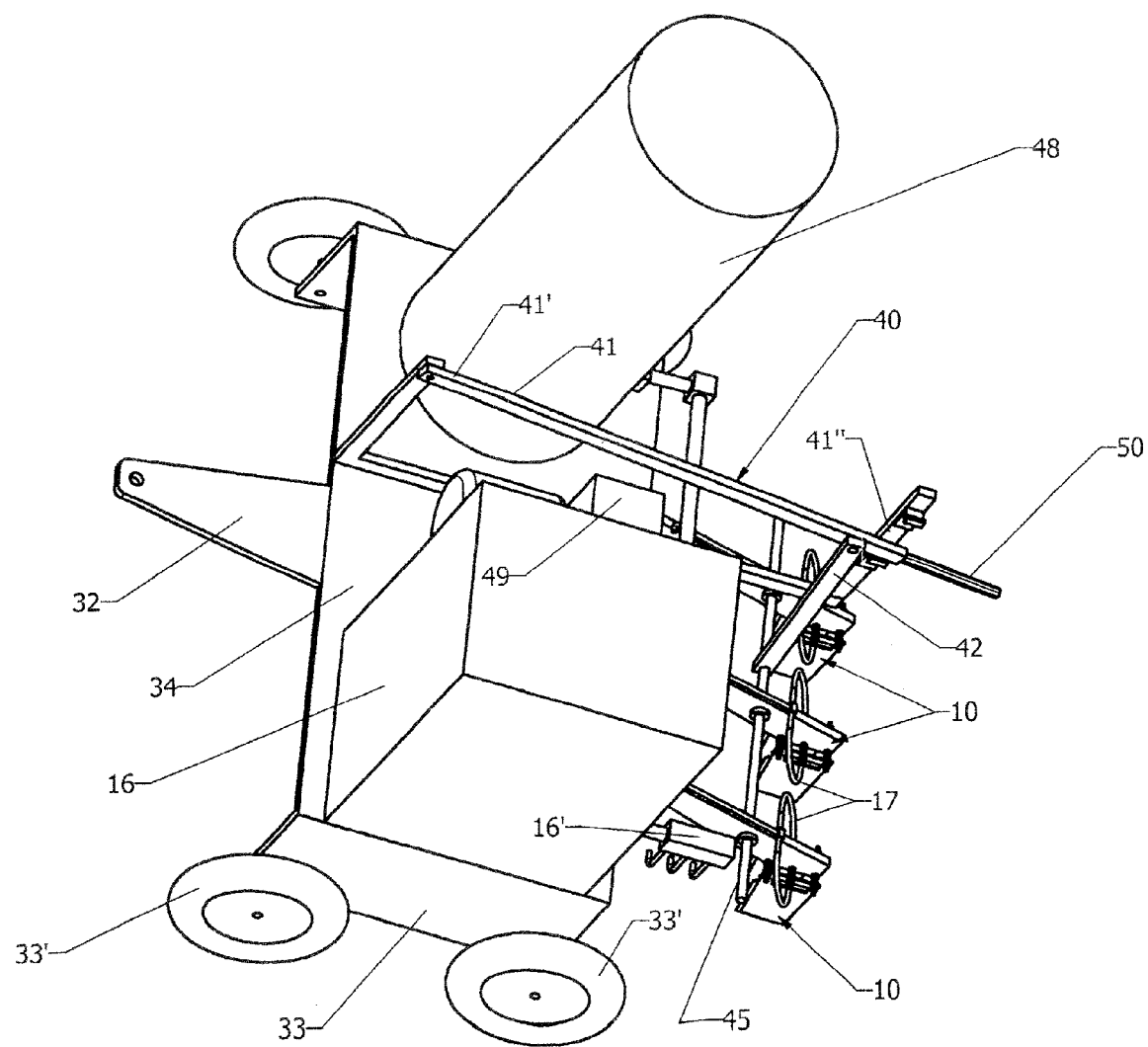
Figure 2:
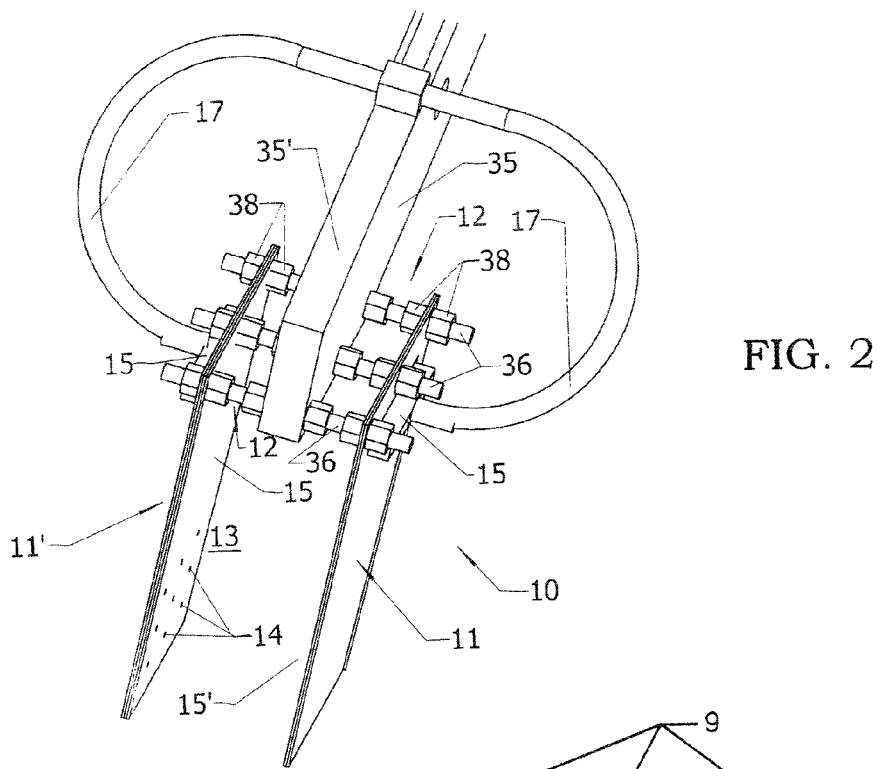
FIG. 2 is an enlarged perspective view of the hot water injecting chamber.
Figure 3:
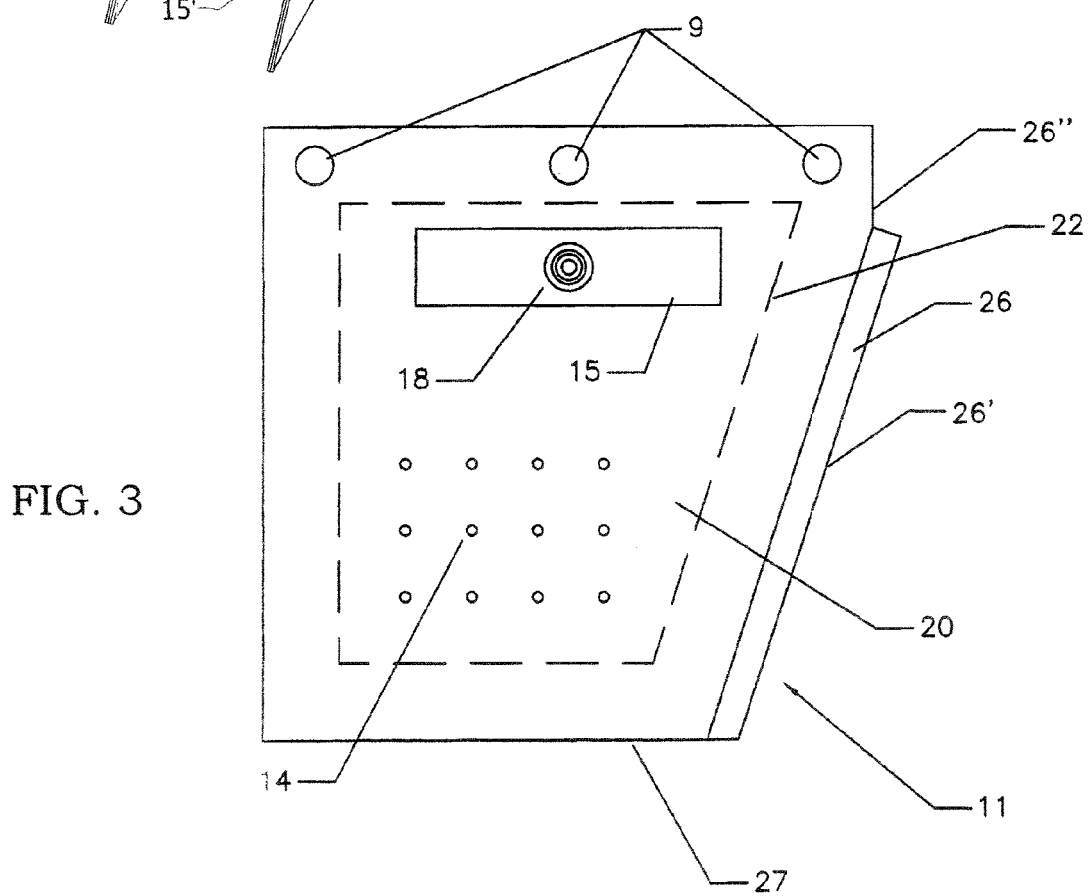
FIG. 3 is a side view of one of the hollow side plates of the hot water injection chamber.
Figure 4:
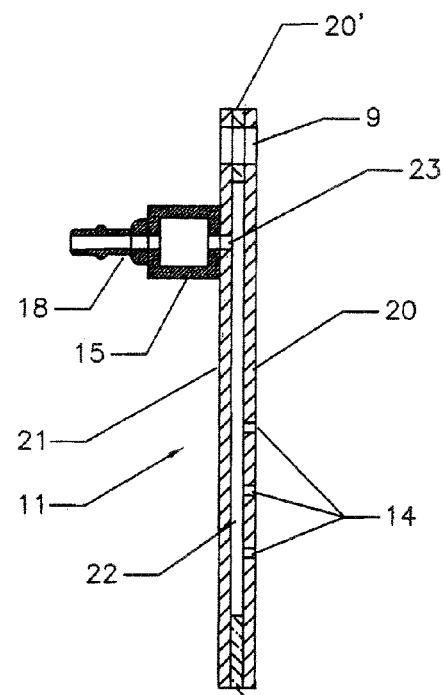
FIG. 4 is a transverse cross view through one of the hollow side plates of the hot water injecting chamber.

Referring to FIGS. 1A and 1B there is shown three hot water injecting chambers 10 constructed in accordance with the present invention and secured to a displaceable carriage 30 which will be described later. The hot water injecting chamber 10 is illustrated in FIGS. 2 to 4 and it is defined by a pair of spaced-apart side walls 11 and 11' secured to one another at a top end portion thereof by an adjustable interconnecting linkage 12 to define therebetween a passage 13. A plurality of jet holes 14 are provided in an inner surface 15 of each of the side walls 11 and 11' and face in the direction of the passage 13. The jet holes 14 communicate with a respective manifold 15 which is connected by flexible conduits 17 to a water heating generator 16 to supply pressurized hot water 16. The flexible conduits 17 are secured to a suitable fitment 18 of their associated manifolds 15. As shown in FIG. 1A the flexible conduit 17, of each hot water injecting chamber 10 is connected to a multi-hose outlet coupling 16' of the hot water generator. A water reservoir 48 provides a supply of water to the hot water generator 16 via a pump 49.

Figure 6:
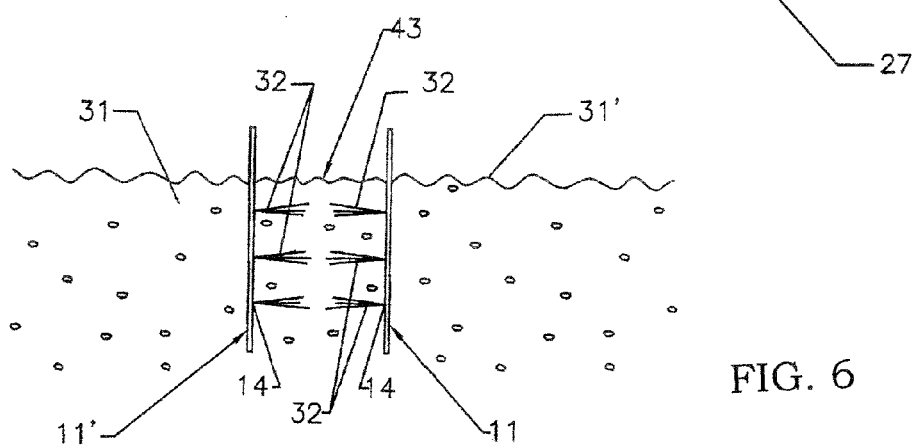
FIG. 6 is a transverse view illustrating the hot water injecting chamber disposed in the soil and saturating the soil with pressurized hot water to form a sterile plant bed.

As shown in FIG. 6, each of the side walls 11 and 11' are configured to penetrate or slice into the soil 31 in at least a lower region thereof where the jet holes are disposed whereby pressurized hot water 32 can be injected into the soil beneath the top surface 31' of the soil to completely saturate the soil between the side walls 11 and 11'.

As shown in FIGS. 2 to 4 the side walls 11 and 11' are hollow side walls formed by a pair of opposed spaced-apart flat plates 20 and 21, namely an inner side plate 20 and outer side plate 21. These plates are sealed to one another about their outer edges by welding or other suitable means such as a contour spacer gasket plate 20' to maintain the plates spaced-apart whereby to define a hollow space 22 therebetween. This hollow space 22 is communicated with its respective manifold 18 through an orifice 23 provided in the outer side wall 21. The plates are stainless steel plates spaced-apart a distance of one sixteenth of an inch. The jet holes 14 are drilled through the inner side wall 20 and communicate with the hollow space 22 whereby hot water under pressure in the manifold is fed in the hollow space and out through the jet holes 14.

As shown in FIGS. 3 and 4, each of the spaced-apart side walls 11 and 11' have a tapered front edge to cut into the soil. This tapered front edge is constituted by a metal bar 26 which has a sharpened front edge 26' and which is welded to a front edge 26" of the spaced-apart side walls. The front edge of the side walls 11 and 11' are also sloped inwardly from a top end portion of the side walls to a straight lower edge 27 of the hollow side plates.

As shown in FIGS. 2 and 3, the top end portion of the opposed side walls 11 and 11' are provided with through holes 9 through which is secured adjustable interconnecting means in the form of an adjustable interconnecting linkage 12. The adjustable interconnecting linkage 12 is comprised by two or more, herein three rods 36 secured to a free end portion 35' of a support arm 35 which is pivotally connected at a pivot end 35" on a support rod 37, see FIG. 5, to the frame 38 of the displaceable carriage 30, shown in FIGS. 1A and 1B. The rods 36 are threaded rods extending through the holes 9 in the side walls 11 and 11' and on which is received nuts 38 to secure the side wails 11 and 11' thereto. The threaded rods 36 and the nuts 38 provide for adjustment of the spacing between the side wails 11 and 11' and thereby the width of the passage 13 forming the planting bed.

Figure 5:
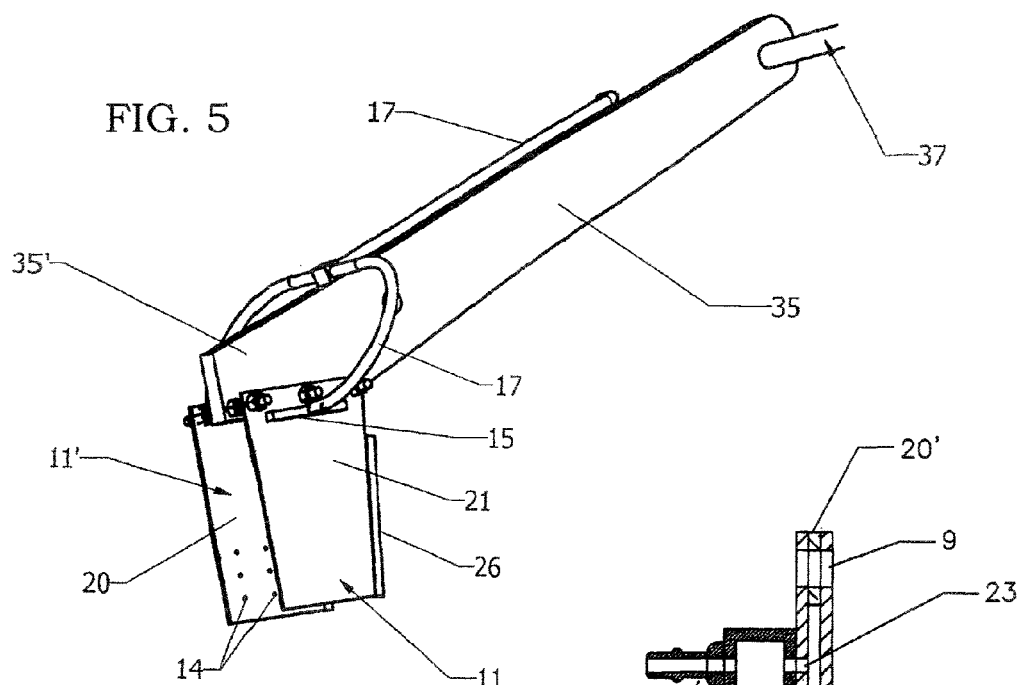
FIG. 5 is a perspective view of the pivotal support arm to which a hot water injecting chamber is secured.

Referring now to FIGS. 1A, 1B and 5 there is shown generally at 30 a typical example of a carriage adapted to be displaced on the surface 31' of a soil 31. The carriage 30 is provided with a frame 38 having opposed spaced-apart vertical wheel support frame members 33 displaceable on wheels 33'. The frame 33 has a top transverse frame member 34. A frame attachment arm 32 provides for connection to a tractor, not shown, for the displacement thereof. As shown, three hot water injecting chambers 10 are secured to the support rod 37 attached to the frame 38 and at an opposed end 41" to the top transverse frame 34. A displaceable support linkage 40 is comprised of a pivotal arm 41 secured at one end to the frame 38 and at an opposed end 41" to a pivotally connecting link arm 42 which permits the water injecting chambers 10 to be positioned from a disengaged position, above the soil surface 31', to an engaged position into the soil surface, as shown in FIG. 6. The link arm 42 is pivotally secured at a lower end to an interconnecting rod 45 adjustably secured to the support arm 35 by suitable means. A handle 50 facilitates adjustment of the pivotal arm 41.

As shown in FIGS. 2 and 6, the jet holes 14 are grouped to be disposed below the top surface 31' on the soil 31 when the water injecting chamber is in the engaged position whereby to saturate the soil with the pressurized hot water 32 injected by the jet holes 14. The displaceable support linkage 40 is interlocked by suitable means when the water injecting chambers are in the engaged position. Also, the spacing between the support arms 35 is adjustable on its support rod 37 to adjust the spacing between the seeding beds 43 (see FIG. 6) being formed by the water injecting chambers as they are pulled in the soil surface.

As shown in FIG. 6 the opposed side walls 11 and 11' are penetrated in the soil surface 31 a distance of approximately 3 inches which is sufficient to locate the jet holes 14 below the soil surface 31 whereby to inject the hot water, which is at a temperature between 150° F. and 200° F. below the soil surface. These jet holes 14 face toward one another into the passage 13 to completely saturate the soil between the side walls 11 and 11'. It has been found that with the carriage 30 being displaced at a rate of about 4 gallons of hot water per 25 feet of bed with the side walls spaced-apart approximately 4 inches that the soil will remain saturated with the hot water for a period of approximately ten minutes which is satisfactory to destroy seeds of unwanted plants or plant roots, the hot water is also dispensed at a pressure sufficient to saturate the soil between the side walls and in the range of about 50 psi to 1000 psi depending on the spacing of the side walls.

Having described the above soil sterilizing apparatus for sterilizing soil to destroy unwanted growth in a planting bed being formed in the soil, the method provides the step of heating water in a hot water generator to a temperature on the range of about 150° F. to 200° F. The apparatus of the present invention is displaced above a top surface of the soil to create planting or seeding beds 43 with the plates 11 and 11' penetrating into the soil while injecting under pressure hot water into the planting bed from opposed sides thereof to destroy weeds, seeds or roots of unwanted growth in the bed being formed. The method also comprises the step of adjusting the distance between the pair of spaced-apart side walls to define the width of the planting bed. The method also permits the adjustment of the distance between the water injecting chambers 10 and therefore the distance between the seeding beds 43 being formed.

All obvious modifications of the present invention are intended to be covered provided they are interpretable within the wording and broad interpretation of the claims.

We claim:

1. An apparatus for sterilizing soil, said apparatus comprising at least one heated water injecting chamber defined by a pair of vertical plates secured spaced-apart to one another and defining between opposed side walls thereof an open-ended passage, a plurality of jet holes in an inner surface of each of said side walls and facing in the direction of said passage, said jet holes communicating with a manifold connectable to a supply of pressurized heated water, each of said pair of plates being configured to penetrate into the soil in at least a lower region thereof to position at least some of said jet holes below a top surface of said soil whereby to inject into the soil, in the passage between said pair of plates, said pressurized heated water as said heated water injecting chamber is displaced along said a top surface of the soil and means to displace said pair of plates penetrated into the soil.

2. An apparatus as claimed in claim 1 wherein said side walls are hollow side walls secured together in a top end portion thereof, said hollow side walls being defined by opposed spaced-apart flat plates which are sealed to each other thereabout, a hollow space defined between said flat plates and communicating with said manifold, said jet holes communicating with said hollow space, and conduit means securable to said manifold to supply said pressurized heated water to said hollow space and said jet holes.

3. An apparatus as claimed in claim 2 wherein said opposed spaced-apart side walls have a tapered front edge to cut into said soil, 4. An apparatus as claimed in claim 3 wherein said tapered front edge is a wedged front edge extending from said top end portion of said side walls to a straight lower edge thereof.

5. An apparatus as claimed in claim 4 wherein said wedged front edge is defined by a metal bar having a sharpened front edge, said metal bar being welded to a front edge of said spaced-apart side walls.

6. An apparatus as claimed in claim 2 wherein said hollow side walls are secured together at said top end portion thereof by an adjustable interconnecting means whereby to adjust the spacing between the said hollow side walls and thereby the width of said passage.

7. An apparatus as claimed in claim 2 wherein said opposed spaced-apart flat plates are stainless steel plates spaced-apart a distance of about one sixteenth of an inch to define said hollow space therebetween.

8. An apparatus as claimed in claim 2 wherein said spaced-apart flat plates define an inner and an outer flat wail of said hollow side wail, said jet holes being disposed in said inner flat wall, said jet holes having a diameter of about one-sixteenth of an inch and provide water jets for said pressurized heated water, said conduit means being secured to a fitment secured to said manifold, and a passageway connecting said manifold to said hollow space.

9. An apparatus as claimed in claim 8 wherein said conduit means is a flexible hose having a connector for detachable securement to said fitment at one end thereof, said flexible hose being secured to a water heating generator supported on displaceable carriage means.

10. An apparatus as claimed in claim 9 wherein said carriage means is provided with one or more support arms pivotally connected at one end to a frame of said carriage, said heated water injecting chamber being connected to a free end of said support arm, and displaceable support means to position said one or more support arms from a disengaged position to an engaged position to position said heated water injecting chamber in and out of engagement with the soil.

11. An apparatus as claimed in claim 10 wherein there are two or more of said heated water injecting chambers secured spaced-apart by two or more of said support arms.

12. An apparatus as claimed in claim 10 wherein said displaceable support means is an adjustable support linkage.

13. An apparatus as claimed in claim 10 wherein said jet holes are grouped such that topmost ones of said jet holes are disposed below a top surface of soil being saturated with said heated, water when said heated water injecting chambers are in said engaged position whereby to destroy seeds of plants in said soil in said passage between said pair of plates.

14. An apparatus as claimed in claim 13 wherein said spaced-apart flat plates have a straight bottom edge, said bottom edge extending into said soil a distance of approximately three inches when displaced therein by said displaceable support carriage means.

* * * * *